United States Patent [19]

Hasegawa et al.

[11] Patent Number: 5,977,360
[45] Date of Patent: Nov. 2, 1999

[54] PROCESS FOR PRODUCING CYCLIC HYDRAZINE DERIVATIVES, TETRA-HYDROPYRIDAZINE AND HEXAHYDROPYRIDAZINE

[75] Inventors: Youichi Hasegawa; Shunji Hyoda; Hiroyuki Fujita; Hirotoshi Sawada; Yasuo Oki, all of Sakaide, Japan

[73] Assignee: Japan Hydrazine Co., Ltd., Japan

[21] Appl. No.: 08/998,168

[22] Filed: Dec. 24, 1997

[30] Foreign Application Priority Data

| Dec. 27, 1996 | [JP] | Japan | 8-351148 |
| Dec. 27, 1996 | [JP] | Japan | 8-351149 |
| Dec. 4, 1997 | [JP] | Japan | 9-334692 |

[51] Int. Cl.$^6$ .................... C07D 237/02; C07D 241/02
[52] U.S. Cl. ..................... 544/164; 546/223; 548/557
[58] Field of Search ............ 548/557; 544/164; 546/223

[56] References Cited

U.S. PATENT DOCUMENTS

| 2,953,570 | 9/1960 | Rudner | 548/557 |
| 3,317,607 | 5/1967 | Latourette | 548/557 |
| 4,202,842 | 5/1980 | Weiner et al. | |
| 4,254,128 | 3/1981 | Weiner et al. | |
| 4,435,600 | 3/1984 | Hasegawa | 564/464 |
| 4,957,905 | 9/1990 | Hunt | 514/29 |
| 5,668,271 | 9/1997 | Kojiri et al. | 548/490 |

FOREIGN PATENT DOCUMENTS

| 0 116 198 A1 | 8/1984 | European Pat. Off. |
| 0 304 920 A2 | 3/1989 | European Pat. Off. |
| 0 693 482 A1 | 1/1996 | European Pat. Off. |

OTHER PUBLICATIONS

Crawford, Robert J., et al., The Synthesis and Physical Properties of Some 1–and 2–Pyrazolines, Journal of the American Chemical Society, vol. 88, 1966, pp. 3959–3963.
JPO Abstract, of JP 81–09120, Apr. 1996.

*Primary Examiner*—Mukund J. Shah
*Assistant Examiner*—Bruck Kifle
*Attorney, Agent, or Firm*—Fulbright & Jaworski L.L.P.

[57] ABSTRACT

The present invention relates to a process for producing alicyclic hydrazine derivatives, tetrahydropyridazine and hexahydropyridazine which are useful as intermediate starting materials such as medicines and agricultural chemicals. Especially, the present invention provides;

a process for producing an alicyclic hydrazine derivative or its hydrohalogenic acid salt, which comprises reacting a hydrazine hydrohalogenic acid salt with a diol compound or an alicyclic ether compound in the presence of an excessive inorganic acid existing in a free form or in the form of an acid addition salt;

a process for producing tetrahydropyridazine from 1-aminopyrrolidine, which comprises oxidizing 1-aminopyrrolidine with an oxidizing agent to form tetrahydropyridazine; and a process for producing hexahydropyridazine, which comprises oxidizing 1-aminopyrrolidine with an oxidizing agent, synthesizing tetrahydropyridazine, and thereafter, hydrogenating the tetrahydropyridazine in the presence of a base.

10 Claims, No Drawings

PROCESS FOR PRODUCING CYCLIC HYDRAZINE DERIVATIVES, TETRA-HYDROPYRIDAZINE AND HEXAHYDROPYRIDAZINE

BACKGROUND OF THE INVENTION

1. Field of the Invention

The present invention relates to a process for producing alicyclic hydrazine derivatives, tetrahydropyridazine and hexahydropyridazine which are useful as intermediate starting materials such as medicines and agricultural chemicals.

2. Description of Prior Art

The present inventors proposed a method for producing tert-butylhydrazine hydrohalogenic acid salt by reacting hydrazine hydrohalogenic acid salt and tert-butanol which are industrially or economically advantageous starting materials (Japanese Patent Publication No. 48823/1986) equivalent to U.S. Pat. No. 4,435,600, issued Mar. 6, 1984 on an application filed Mar. 10, 1983.

However, it has not yet been known that a difunctional alcohol (diol) or an alicyclic ether compound reacts with a hydrazine hydrohalogenic acid salt to give an alicyclic hydrazine derivative hydrohalogenic acid salt.

As a method for producing an alicyclic hydrazine derivative or its hydrohalogenic acid salt, there are known a method of reacting an alkyl dihalide with hydrazine hydrate [USSR Pat. 87-4337106], [J. Am.Chem. Soc. 88, 3959–3963 (1966)] (prior art 1), and a method of synthesizing alicyclic hydrazine by using an alicyclic amine as a starting material [U.S. Pat. No. 3,317,607] (prior art 2).

However, the prior art 1 relating to a method of producing an alicyclic hydrazine derivative or its hydrohalogenic acid salt has a problem that an economically expensive dihalogenobutane is required as a starting material. Furthermore, the prior art 2 is a general method of synthesizing alicyclic hydrazine, but the stability and toxicity of the nitroso body which is an intermediate pose a problem.

On the other hand, a known conventional method of synthesizing hexahydropyridazine includes reacting a hydrazine dicarboxylic derivative with a dihalogenobutane to obtain hexahydropyridazine-1,2-dicarboxylic derivative, and further decarboxylating the resulting product to give an intended product [Japanese Laid-Open Patent Publication Nos. 224043/1995, 224044/1995 and 198853/1996] (prior art 3).

A method of producing hexahydropyridazine which comprises synthesizing tetrahydropyridazine from 1,4-butanedial and hydrazine and hydrogenating this tetrahydropyridazine is also known [Japanese Laid-Open Patent Publication No. 109170/1996] (prior art 4).

As a method for producing tetrahydropyridazine from 1-aminopyrrolidine, there is known a method comprising carrying out a rearrangement reaction of diazenehydrazone on silica or alumina in, for example, a chloroform-methanol solvent [Tetrahedoron Letters, No. 52, pp. 5025 to 5026] (prior art 5). Furthermore, a method comprising leaving 1-aminopyrrolidine to stand at room temperature in chloroform for 2 weeks is also known [Japanese Laid-Open Patent Publication No. 250388/1989], [Chem. Ber., 109, (11), 3707 (1976)] (prior art 6).

However, the prior art 3 relating to a method for producing hexahydropyridazine has a problem that the dihalogenobutane as a starting material is economically expensive, and the synthetic route up to the product is long.

On the other hand, in the prior art 4, 1,4-butanedial used as a starting material is not easily available, and the yield is as low as about 60%.

Furthermore, the prior art 5 relating to a method for producing tetrahydropyridazine conducts a oxidation and rearrangement reaction of the starting material while it is adsorbed on silica or alumina. However, the after-treatment after the reaction is complicated. Furthermore, in the prior art 6, the reaction time is long, and it is inadequate as an industrial method for producing tetrahydropyridazine.

SUMMARY OF THE INVENTION

The present invention dissolves the defects of the conventional techniques, and makes it an object of providing a method of producing an alicyclic hydrazine derivative or its hydrohalogenic acid salt industrially and economically advantageously from an inexpensive starting material which is easy to handle, namely a diol compound or an alicyclic ether compound.

It is another object of the present invention to provide a method of producing hexahydropyridazine which is economically and industrially advantageous. In the present invention, in comparison with the prior art, hexahydropyridazine can be obtained with high selectivity from cheap and easily handlable starting materials.

Another object of the present invention is to provide a method of producing tetrahydropyridazine which becomes an intermediate of synthesizing hexahydropyridazine with high selectivity from cheap and easily handlable starting materials.

The present invention provides a method for producing an alicyclic hydrazine derivative or its hydrohalogenic acid salt which comprises reacting a hydrazine-hydromonohalogenic acid salt and a diol compound or an alicyclic ether compound in the presence of an excessive inorganic acid present in a free form or in the form of an acid addition salt.

The present invention also provides a method for producing hexahydropyridazine which comprises hydrogenating tetrahydropyridazine, wherein the tetrahydropyridazine is hydrogenated in the presence of a base.

The present invention further provides a method for producing tetrahydropyridazine from 1-aminopyrrolidine, which comprises oxidizing 1-aminopyrrolidine with an oxidizing agent to form tetrahydropyridazine.

The present invention further provides a method for producing hexahydropyridazine which comprises oxidizing 1-aminopyrrolidine with an oxidizing agent to synthesize tetrahydropyridazine, and then hydrogenating the tetrahydropyridazine in the presence of a base.

According to one embodiment of the present invention, there is provided a method for producing hexahydropyridazine, which comprises reacting hydrazine hydrohalogenic acid salt with butanediol or tetetrahydrofuran to synthesize 1-aminopyrrolidine, and then oxidizing 1-aminopyrrolidine with an oxidizing agent to synthesize tetrahydropyridazine, and thereafter hydrogenating the tetrahydropyridazine in the presence of a base.

DETAILED DESCRIPTION OF PREFERRED EMBODIMENT

In the first embodiment of the present invention, it is desired that 1. the hydrazine hydrohalogenic acid salt is a hydrazine hydromonohalogenic acid salt expressed by the formula (1)

$$NH_2NH_2 \cdot HX \qquad (1)$$

wherein X represents a halogen atom;
2. the diol compound is a diol compound expressed by the following formula (2)

$$HO-(CH_2)_m-A-(CH_2)_n-OH \qquad (2)$$

wherein A represents an oxygen atom, a methylene group or an ethylidene group, and m and n are integers of 1 to 3;
3. the alicyclic ether compound is an alicyclic ether compound shown by the formula (3)

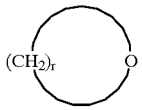
(3)

wherein r is an integer of 4 or 5.
4. the alicyclic hydrazine derivative is an alicyclic hydrazine derivative expressed by the formula (4)

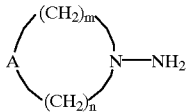
(4)

wherein A represents an oxygen atom, a methylene group or an ethylidene group, and m and n are integers of 1 to 3,
or expressed by the formula (5)

(5)

wherein p is an integer of 3 or 4;
5. the excessive inorganic acid is a hydrohalogenic acid or its salt.
6. the excessive inorganic acid is present in the form of a hydrazine hydrodihalogenic acid or its salt.
7. the reaction is carried out at a temperature of 100 to 150° C. under an elevated pressure while the mole ratio of the diol compound or the alicyclic ether compound:hydrazine hydromonohalogenic acid salt:excessive inorganic acid is 1:1–10:0.2–3.

The reaction solution obtained by the above method is concentrated, and an alcohol solvent, etc. is added. The unreacted hydrazine hydrohalogenic acid salt precipitated as a crystal is removed in a customary manner. Then, the separated mother liquor is subjected to an ordinary method such as dilution or cooling, whereby an alicyclic hydrazine derivative hydrohalogenic acid salt precipitated as a crystal can be separated and recovered. Furthermore, the above separated mother liquor is neutralized with a base, and distilled to give an alicyclic hydrazine derivative.

In the present invention, the diol compound or the alicyclic ether compound is reacted with the hydrazine hydrohalogenic acid salt in the presence of an excessive inorganic acid to give an alicyclic hydrazine derivative at once. In this regard, the reaction of the present invention is novel and peculiar.

The diol compound or the alicyclic ether compound, together with the hydrazine-hydrohalogenic acid salt, is a starting material which is easily available and cheap. In addition, since the handlability of these materials is easy during the reaction, the invention can provide the alicyclic hydrazine derivative or its hydrohalogenic acid salt industrially advantageously.

The excessive inorganic acid may be present in a free form or in the form of an acid addition salt. Hydrohalogenic acids are preferred as the inorganic acid. In this case, the hydrohalogenic acids may exist in the form of hydrazine hydrohalogenic acid. As the hydrohalogenic acids, hydrochloric acid and hydrobromic acid are preferred.

As the hydrazine hydrohalogenic acid salt, hydrochloride salt and hydrobromide salt may be used. The hydrochloride salt is preferred. The hydrazine hydrohalogenic acid salt shown in the formula (1), namely hydrazine hydromonohalogenic acid salt, is preferred. The hydrazine hydrohalogenic acid salt may be relatively pure, or may contain an impurity. For example, the hydrazine hydrohalogenic acid salt recovered from the mother liquor may be repeatedly used in the reaction. Of course, the hydrazine hydrodihalogenic acid salt used may be used as a starting material for hydrazine.

The diol compound may be any compound which is an aliphatic compound having two hydroxyl groups. The number of carbons in the diol compound may be 3 to 8. The hydroxyl groups may be primary, secondary or tertiary hydroxyl groups, but in respect of the reactability, a primary hydroxyl group is preferred. The skeleton of the diol compound may be a straight chain alkylene group or a branched chain alkylene group. In this alkylene chain, atoms other than carbon, such as an ether oxygen atom, may be interposed.

Suitable diol compounds may be those represented by general formula (2). Proper examples include 1,3-propanediol, 1,4-butanediol, 1,5-pentanediol, 1,6-hexanediol, 3-methyl-1,5-pentanediol and diethyleneglycol.

In the present invention, alicyclic ether compounds may be used instead of the diol compounds. As the alicyclic ether compounds, compounds having 4 to 5 carbon atoms and containing at least one ether oxygen atom within the ring are used. Alicyclic ether compounds expressed by general formula (3) are preferred. Proper examples include tetrahydrofuran and tetrahydropyran. Tetrahydrofuran is most preferred.

According to the present invention, the hydrazine hydrohalogenic acid salt is reacted with the diol compound or the alicyclic ether compound in the presence of an excessive inorganic acid to form an alicyclic hydrazine derivative in the form of a hydrohalogenide salt.

This reaction includes two cases of reactions, namely, that one nitrogen atom in the hydrazine is taken into the ring (reaction A), and that two nitrogen atoms in the hydrazine are taken into the ring (reaction B). These cases will be illustrated below.

(1) Reaction A

When 1,4-butanediol or tetrahydrofuran is reacted with hydrazine hydrohalogenic acid salt in the presence of an inorganic acid, 1-aminopyrrolidine hydrohalogenic acid salt will be formed as shown in the following formula (6).

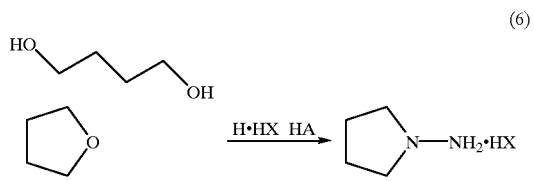

(6)

When 1,5-pentanediol or tetrahydropyran is reacted with hydrazine hydrohalogenic acid salt in the presence of an inorganic acid, 1-aminopiperidine hydrohalogenic acid salt will be formed as shown by the formula (7).

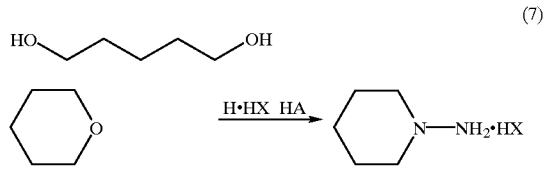

(7)

When 3-methyl-1,5-pentanediol is reacted with hydrazine hydrohalogenic acid salt in the presence of an inorganic acid, 1-amino-4-methylpiperidine hydrohalogenic acid salt will be formed as shown in the formula (8).

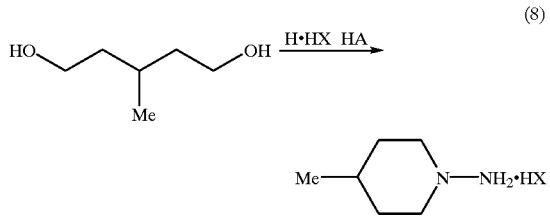

(8)

When 1,6-hexanediol is reacted with a hydrazine hydrohalogenic acid salt in the presence of an inorganic acid, 1-aminohexamethyleneimine hydrohalogenic acid salt will be formed as shown by the formula (9).

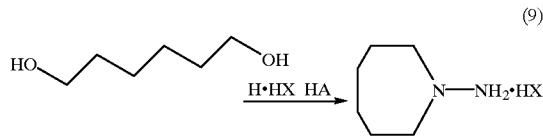

(9)

When diethylene glycol is reacted with a hydrazine hydrohalogenic acid salt in the presence of an inorganic acid, a 4-aminomorpholine hydrohalogenic acid salt will be formed as shown by the formula (10)

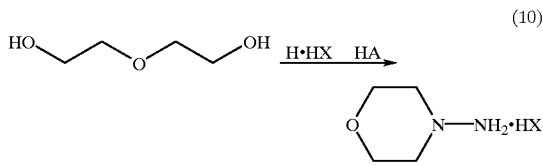

(10)

(2) Reaction B

When 1,3-propanediol is reacted with a hydrazine hydrohalogenic acid salt in the presence of an inorganic acid, a pyrazolidine hydrohalogenic acid salt will be formed as shown by the formula (11).

(11)

As will be described later, when 1,4-butanediol is used as the starting material, it is recognized that hexahydropyridazine is also formed although its yield is low.

In the present invention, the mole ratio of the diol compound or alicyclic ether compound: the hydrazine hydromonohalogenic acid salt (H.HX): the excessive inorganic acid (HA) is 1:1–10:0.2–3. Preferably, this mole ratio is 1:2–5:1–2.

The reaction temperature is 100 to 150° C., preferably 110 to 140° C. The reaction pressure is normal pressure to 10 $Kg/cm^2G$, preferably about 2 to 8 $Kg/cm^2G$. The reaction time differs depending upon the intended alicyclic hydrazine derivative but is about 1 to 30 hours. In the case of reaction A, when the product is a 1-aminopyrrolidine hydrohalogenic acid salt, the reaction time is 3 to 10 hours.

Water can be used as the solvent. Industrially, a method will be available in which H.HX, the diol compound or the alicyclic ether compound, and the excessive inorganic acid, or H.HX, the diol compound or the alicyclic ether compound and the hydrazine hydrodihalogenic acid salt are simultaneously charged in a reaction vessel and used in the reaction. Another method is to add the diol compound or the alicyclic ether compound, and the inorganic acid to the H.HX aqueous solution prepared from a hydrazine hydrate and a hydrohalogenic acid.

In this reaction, to use H.HX in an excessive amount to the diol compound or the alicyclic ether compound, H.HX must be separated from the alicyclic hydrazine derivative hydrohalogenic acid salt in order to obtain the alicyclic hydrazine derivative hydrohalogenic acid salt having a high purity. For that purpose, water used as the solvent is concentrated and an alcohol solvent such as methanol is added, and then the H.HX is crystallized and thereafter taken out as a crystal. It is then separated from the intended alicyclic hydrazine derivative hydrohalogenic acid salt. When by one operation, H.HX cannot be fully removed from the reaction solution, the separating operation of H.HX may better be repeated several times.

The reaction residue from which H.HX has been removed is left to stand at room temperature whereby the alicyclic hydrazine derivative hydrohalogenic acid salt can be isolated as a crystal.

Furthermore, the isolated alicyclic hydrazine derivative hydrohalogenic acid salt crystal was neutralized with a base such as sodium hydroxide and precisely distilled to obtain the desired alicyclic hydrazine derivative.

The reaction solution after separating H.HX is neutralized with a base such as sodium hydroxide, the resulting inorganic salt was separated by filtration, and the filtrate was precisely distilled whereby the desired alicyclic hydrazine derivative could be isolated.

The amounts of by-products at the time of synthesizing the alicyclic hydrazine derivative hydrohalogenic acid salt are small, and the reaction selectivity is high.

For example, when 1,4-butanediol is reacted with hydrazine monohydrochloride salt in the presence of hydrochloric acid to produce 1-aminopyrrolidine hydrochloride salt, the by-products are shown in the following formula (12).

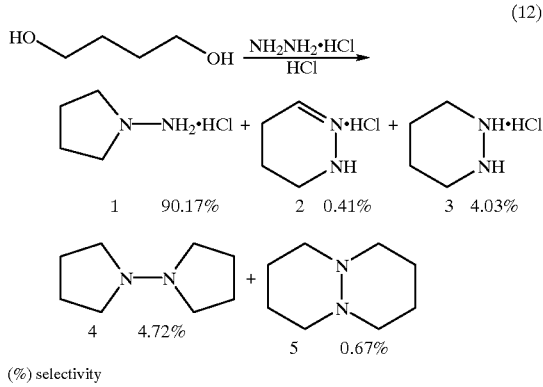

(12)

(%) selectivity

Based on an analysis of gas chromatography, four by-products and the reaction selectivity are shown. The 1-aminopyrrolidine 1 showed a high selectivity of more than 90%. The structures of these by-products were identified or assumed. Tetrahydropyridazine 2 and hexahydropyridazine 3 were compared and identified by GC with a standard sample. Since the other two by-products had a molecular weight of 140 by GC-MS analysis, they were assumed to be 1,1-bipyrrolidine 4 produced by the reaction of 1-aminopyrrolidine and 1,4-butanediol and also to be octahydropyridazino[1,2-a]pyridazine 5 formed by reaction of hexahydropyridazine 3 and 1,4-butanediol.

The outline of the reaction mechanism is shown in the following formula (13). Especially, it has been found that 1-aminopyrrolidine hydrochloric acid salt is obtained peculiarly with a high selectivity and in a high yield.

The production of hexahydropyridazine by hydrogenating tetrahydropyridazine is a known fact as recognized in the prior art 2. But according to the method of the prior art 2, the reaction takes as long as 8 days, and in addition, the yield is as low as about 60%.

In contrast, according to the present invention, by hydrogenating tetrahydropyridazine in the presence of a base, the reaction speed increases and the reaction time can be shortened to about 6 hours. At the same time, the conversion of tetrahydropyridazine can be increased to at least 90%, and the selectivity into hexahydropyridazine can be increased to at least 90%.

Furthermore, in a conventional synthesizing method of producing tetrahydropyridazine by diazene-hydrazone rearragement of 1-aminopyrrolidine, 1-aminopyrrolidine is adsorbed in silica or alumina or is reacted in chloroform. However, the reaction time is long, and the operation is complicated.

In contrast, the method of the present invention comprises oxidizing 1-aminopyrrolidine with an oxidizing agent whereby the conversion of 1-aminopyrrolidine is increased to at least 90% and the selectivity into tetrahydropyridazine is increased to about 60% or more, and in addition, a treatment after the reaction is not necessary. The method of the present invention is excellent in these regards.

When the oxidation is carried out by using air or oxygen in the presence of an inorganic base, the by-product during the production is only pyrrolidine, and in addition, since the co-existing inorganic base suppresses the by-production of pyrrolidine, the reaction is extremely convenient.

The whole reactions of this invention are shown by the formula (14).

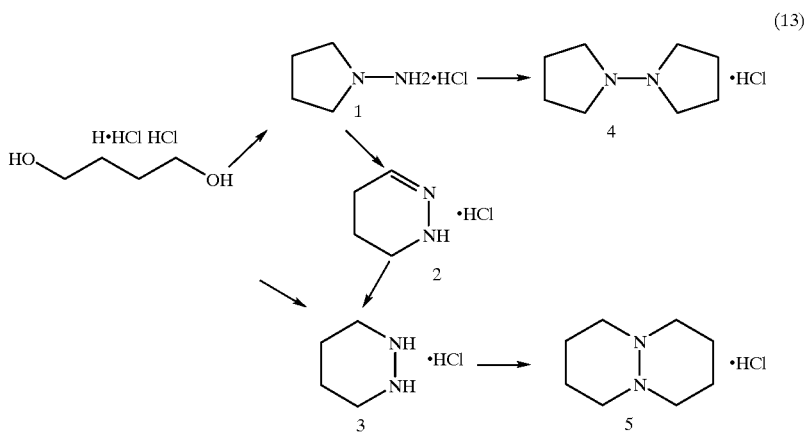

(13)

In the hydrogenation of tetrahydropyridazine in the present invention, it is preferred that:
1. the base is sodium hydroxide and/or potassium hydroxide.
2. the hydrogenation is carried out in the presence of a noble metal catalyst.
3. the hydrogenation is carried out at a temperature of room temperature to 120° C. under a pressure of normal pressure to 100 Kg/cm²G.

Furthermore, the oxidation of 1-aminopyrrolidine to tetrahydropyridazine is preferred carried out in a polar solvent at a temperature of 200° C. or below, especially at room temperature to 100° C. so that the mole ratio of the oxidizing agent to 1-aminopyrrolidine becomes at least 1.0.

(14)

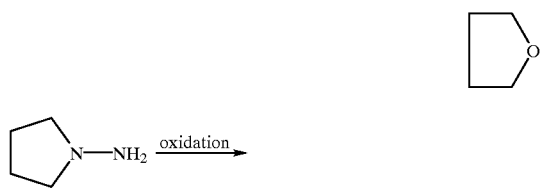

-continued

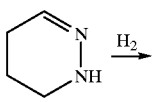

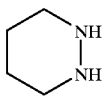

The reaction in the first stage has been already mentioned before. By oxidizing 1-aminopyrrolidine with an oxidizing agent, diazene-hydrazone rearrangement occurs to form tetrahydropyridazine. This tetrahydropyridazine is hydrogenated in the presence of a base to form hexahydropyridazine. In the following, the above reaction will be explained in this sequence.

1-Aminopyrrolidine prepared by various methods can be used. Its purity is desirably as high as possible. But it may contain by-products formed in the synthetic process or the solvent so long as these substances do not hinder the reactions of the present invention. 1-Aminopyrrolidine may be used in the form of a hydrohalogenic acid salt.

As explained above, the hydrazine.hydrohalogenic acid salt is reacted with the diol compound or the alicyclic ether compound. The 1-aminopyrrolidine hydrohalogenic acid salt obtained by this reaction or 1-aminopyrrolidine hydrohalogenic acid salt solution containing the mother liquor obtained in this reaction may be used as a synthesizing starting material of tetrahydropyridazine.

The form of the solution which may be taken in oxidizing 1-aminopyrrolidine with an oxidizing agent is as follows.

1. A solution in a polar solvent of 1-aminopyrrolidine or its hydrohalogenic acid salt. For example, it is a solution in methanol, ethanol, isopropyl alcohol, tetrahydrofuran or water.

2. A solution of 1-aminopyrrolidine hydrohalogenic acid salt containing the mother liquor which is obtained by the reaction of the doil compound or the alicyclic ether compound with hydrazine hydrohalogenic acid.

Examples of the oxidizing agent include oxygens such as air, oxygen and ozone; inorganic or organic peroxides such as aqueous hydrogen peroxide, sodium peroxide, barium peroxide and benzoyl peroxide; inorganic or organic peracids or peracid-salts such as potassium persulfate (potassium peroxodisulfate), potassium hydrogen persulfate (potassium hydrogenperoxosulfate), sodium persulfate, barium persulfate, percarbonate salt, perborate salt, performic acid, peracetic acid, perbenzoic acid, trifluoro-peracetic acid and m-chloro-perbenzoic acid; halogens such as chlorine, bromine, fluorine and iodine; halogen-oxy acid or its salts such as hypohlorous acid or its salts, chloric acid or its salts and perchloric acid or its salts; permanganic acid or its salts; and chromic acid or its salts.

Among these oxidizing agents, air or oxygen is cheap in the cost of the oxidizing agent. The oxidizing reaction occurs only by blowing air or oxygen in the reaction system, and the operation is simple. Furthermore, no foreign matter comes into the reaction system. Moreover, the selectivity of 1-aminopyrrolidine to tetrahydropyridazine can be advantageously increased to at least 60% or more.

The oxidation reaction of 1-aminopyrrolidine with air or oxygen can be promoted in the presence of an inorganic base such as sodium hydroxide and/or potassium hydroxide. When the oxidation reaction is carried out for a long period of time by adding an inorganic base, the reaction speed becomes gradually slow if the amount of the base added is small. At such a time, by again adding the inorganic base newly, the speed of the reaction can be increased.

The suitable amount of the inorganic base added is 5 to 100 mole %, especially 10 to 50 mole %, based on 1-aminopyrrolidine. When the inorganic base is not added, or it is added in a smaller amount, the amount of the by-product pyrrolidine increases.

If a method of oxidizing with molecular oxygen or air is used, the reaction temperature may be from room temperature to 100° C., preferably 40 to 80° C., and the reaction time required is 10 to about 150 hours.

Air or oxygen is blown into a solution of 1-aminopyrrolidine in a polar solvent, and the oxidation reaction is carried out. The amount of air required is about 3 to 30 times the charged mole number of 1-aminopyrrolidine.

When in the present invention a peroxide such as aqueous hydrogen peroxide, a peracid such as m-perbenzoic acid or a halogen such as chlorine is used, it is possible to shorten the reaction time drastically, and the productivity can be increased. In a method of using an oxidizing agent such as air or oxygen, the reaction time required will be generally about 40 to 60 hours. But in the case of using aqueous hydrogen peroxide, the reaction time can be within 30 hours, especially within 12 hours until the reaction is completed, and the reaction has excellent productivity. When an organic solvent such as methanol is used as a solvent, there is no likelihood of producing a detonating gas with oxygen and the reaction has excellent safety.

When an oxidizing agent such as aqueous hydrogen peroxide is used, the reaction temperature is 200° C. or below, preferably 40 to 100° C. When the oxidation reaction of 1-aminopyrrolidine with aqueous hydrogen peroxide is carried out at a low temperature such as 0° C., the reaction may run away owing to an abrupt heat generation, and special care should be taken about the handling. However, under the above-mentioned heating conditions, the heat generation is only slight, and it is easy to control the reaction. Furthermore, a reaction time of within 30 hours is required.

An oxidizing agent such as aqueous hydrogen peroxide is added to a solution of 1-aminopyrroliding in a polar solvent and the oxidation reaction is carried out. The amount of the oxdizing agent required is at least 1.0 times, preferably about 1.1 to 3.0 times the charged mole number of 1-aminopyrrolidine. When aqueous hydrogen peroxide is used, its concentration is about 3 to 35%.

When about 90% of the exessive amount of the hydrazine hydrohalogenic acid salt is recovered from the reaction solution of 1-aminopyrrolidine hydrohalogenic acid salt, and after neutralization, 1-aminopyrrolidine is recovered quantitatively by simple distillation, the content of hydrazine hydrate in the fraction decreases in comparison with the neutralization solution, but the hydrazine hydrate remains in the fraction in an amount of about 3 to 5 mole % based on the 1-aminopyrrolidine. When an oxidizing agent such as aqueous hydrogen peroxide is added to the neutralization solution in which a small amount of hydrazine hydrate remains or to the simple distillation fraction to perform an oxidation reaction, the hydrazine hydrate is oxidized and decomposed. In this case, an abrupt heat generation is not observed, and it is easy to control the oxidation reaction. Furthermore, since octahydropyridazino[1,2-a]pyridazine, and 1,1-bipyrrolidine formed as by-products in a synthesizing reaction of forming 1-aminopyrrolidine hydrohalogenic acid salt are oxidized and decomposed, it is possible to to supply tetrahydropyridazine having a high purity.

[Synthesis of hexahydropyridazine]

According to the present invention, tetrahydropyridazine is hydrogenated in the presence of a base to form hexahydropyridazine. The hydrogenating reaction may be preferably carried out by using a noble metal catalyst.

It is important in the present invention that the catalytic hydrogenation reaction is carried out in the presence of a base. Preferred bases include inorganic bases such as sodium hydroxide and potassium hydroxide. As an example, when hydrogenation is carried out in the presence of sodium hydroxide, the conversion:90%, selectivity:hexahydropyridazine 87%, 1-aminopyrrolidine 3%, and 8% of tetrahydropyridazine remained (GC analysis). The reaction selectivity of hexahydropyridazine rises strikingly. Under the reaction conditions, even a reducing reaction at a high temperature may suppress a decomposition reaction to pyrrolidine as compared with the absence of a base, and the speed of the reaction is increased.

The suitable amount of the base is 2 to 65 mole %, especially 6 to 20 mole %, based on tetrahydropyridazine. When a base is not added, or if the amount of the base is smaller than that mentioned above, the conversion or the selectivity decreases drastically.

The catalytic hydrogenating reaction of tetrahydropyridazine using a noble metal catalyst gives a by-product of 1-aminopyrrolidine which is a starting material for tetrahydropyridazine in addition to hexahydropyridazine as a desired product. The reaction formula is shown by the following formula (15).

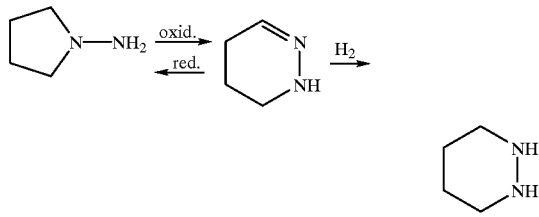

(15)

As already stated, tetrahydropyridazine is formed by an oxidation reaction of 1-aminopyrrolidine, and its reverse reaction is thought to occur; namely there is thought a reaction mechanism in which 1-aminopyrrolidine is formed as a by-product from tetrahydropyridazine by a reducing reaction. It is thought that the addition of the base will suppress this reverse reaction.

Examples of the noble metal catalyst used in the hydrogenation include catalysts containing platinum, palladium, rhodium, ruthenium, etc. as an active component. The metal or metal oxide which is carried on a carrier such as active carbon, alumina, silica gel or diatomaceous earth used. Pt or Pd carried on active carbon is preferred.

Tetrahydropyridazine desirably have a high purity, but insofar as it does not impede the reaction of the present invention, it may contain the by-products and the solvent in the synthetic process.

The reaction temperature is room temperature to 180° C., preferably 50 to 150° C. When the reaction temperature is increased, pyrrolidine as a decomposition product increases. The reaction time is 1 to 120 hours and the reaction pressure is normal pressure to 100 Kg/cm$^2$G. As the noble metal catalyst, a noble metal catalyst having a concentration of 0.05 to 1.5% by weight based on tetrahydropyridazine (metal basis) is used. As the reaction solvent, alcohol solvents such as methanol, ethanol and isopropyl alcohol are preferred.

The 1-aminopyrrolidine formed as a by-product may be converted to tetrahydropyridazine by oxidizing it with an oxidizing agent, and again used in the reducing reaction.

After the solvent is recovered from a reaction solution of hexahydropyridazine obtained by catalytic hydrogenation of tetrahydropyridazine using a noble metal catalyst, the desired hexahydropyridazine can be isolated by precise distillation.

According to the present invention, by reacting hydrazine hydrohalogenic acid salt with a diol compound or an alicyclic ether compound in the presence of an excess of an inorganic acid, alicyclic hydrazine derivatives useful as intermediates of medicines or agricultural chemicals may be produced with industrial or economical advantage.

Furthermore, according to the present invention, when tetrahydropyridazine is hydrogenated in the presence of a base, the reaction speed can be increased and the reaction time can be shortened drastically, and it is possible to increase the conversion of tetrahydropyridazine to at least 90% and the selectivity to hexahydropyridazine to at least 90%.

Moreover, by oxidizing 1-aminopyrrolidine with an oxidizing agent, the conversion of 1-aminopyrrolidine can be increased to at least 90%, and the selectivity to tetrahydropyridazine can be increased to at least about 60% or more. It is excellent that the reaction time can be shortened considerably, and an after-treatment is not necessary. When oxidation is carried out by using an oxidizing agent, the by-product during the production is only pyrrolidine. In addition, since impurities existing in the starting 1-aminopyrrolidine can be decomposed by oxidation, it is extremely convenient.

Thus, 1-aminopyrrolidine is synthesized from hydrazine hydrohalogenic acid salt and butane diol or tetrahydrofuran, and by oxidizing 1-aminopyrrolidine with an oxidizing agent to form tetrahydropyridazine, and next, the tetrahydropyridazine is hydrogenated by using a noble metal catalyst to produce with industrial and economical advantages hexahydropyridazine which is very useful as an intermediate for agricultural chemicals or medicines.

EXAMPLES

The present invention will be specifically explained by the following Examples, but the present invention is not limited to these Examples.

Analysis of alicyclic hydrazine derivatives including 1-aminopyrrolidine, tetrahydropyridazine and hexahydropyridazine has been conducted by gas chromatography, or neutralization titration using hydrochloric acid or sodium hydroxide.

The crystal obtained after concentrating the reaction solution, which is obtained by reacting the hydrazine hydrohalogenic acid salt with the diol compound or the alicyclic ether compound, is a mixture of H.HX and H.2HX, but it is expressed by seeking the amount corresponding to H.HX by a titration analysis. The recovery rate of H.HX is calculated based on a value obtained by subtracting the charge amount of a reaction substrate from the amount corresponding to H.HX.

Example 1

Synthesis of 1-aminopyrrolidine hydrochloric acid salt

A 1-liter glass autoclave was charged with 226.1 g (3.30 moles) of hydrazine monohydrochloride, 111.4 g (1.10 moles) of concentrated hydrochloric acid, 99.1 g (1.10 moles) of 1,4-butanediol and 330.0 g of H$_2$O. With stirring, they were reacted at 140° C. and under 2.2 to 5.6 Kg/cm$^2$G for 5 hours. After the reaction, the reaction solution was concentrated under reduced pressure, and a mixture of (hydrazine monohydrochloride+hydrazine dihydrochloride) was washed with methanol to separate 179.9 g of the product as a crystal. The mixture had a composition which was determined by titration with 1N-NaOH and contained 77.40% by weight [139.24 g (2.03 mols), recovery rate 92.27%] of hydrazine monohydrochloride and 20.82% by weight [37.46 g (1.03 mols), recovery rate 93.29%] of HCl.

Methanol (20 g) was added to 162.0 g of the reaction methanol solution concentrated. The mixture was allowed to stand at room temperature to give 79.8 g of a white primary crystal of 1-aminopyrrolidine hydrochloric acid salt. (Content: titrated 101.87%, GC 99.66% (0.65 mole) was isolated.) Furthermore, the separated mother liquor was concentrated to give 23.9 g of a white secondary crystal of 1-aminopyrrolidine hydrochloric acid salt. (Content: titrated 96.88%, GC 94.53% (0.19 mole) was isolated.) The yield of 1-aminopyrrolidine hydrochloric acid salt crystal was 76.40%. The separated mother liquor contained 58.57% by weight of 1-aminopyrrolidine hydrochloric acid salt remaining therein. The total yield of 1-aminopyrrolidine hydrochloric acid salt was 87.4%. Furthermore, 1,4-butanediol did not remain (GC analysis).

Incidentally, the identification of 1-aminopyrrolidine was performed by showing that the holding-time of a standard sample of 1-aminopyrrolidine agreed with the holding time of GC and by following NMR $^1$H-NMR (a mixed solvent comprising DMSO-$d_6$ and $CDCl_3$); 1.83–2.26 (m, 4H, —$CH_2$—); 3.23–3.67 (m, 4H, —$CH_2$—); 7.88 (bs, 3H, —$NH_2$, HCl)~D exchangeable Example 2
Synthesis of 1-aminopyrrolidine hydrochloric acid salt A 1-liter glass autoclave was charged with 150.7 g (2.20 moles) of hydrazine monohydrochloride, 115.5 g (1.10 moles) of hydrazine dihydrochloride, 99.1 g (1.10 moles) of 1,4-butanediol, and 401.3 g of $H_2O$. With stirring, they were reacted at 140° C. for 3 hours.

After the reaction, the reaction solution was concentrated under reduced pressure, and a mixture (hydrazine monohydrochloride+hydrazine dihydrochloride) was washed with methanol to separate 183.0 g of a crystal. The composition of the mixture was titrated with 1N-NaOH and contained 77.92% by weight [142.59 g (2.08 mols), recovery rate 94.61%] of hydrazine monohydrochloride and 19.72% by weight[36.09 g (0.99 mol), recovery rate 89.88%] of HCl.

Methanol (20 g) was added to the concentrated reaction solution, and 149.6 g of the methanol solution of the concentrated reaction solution was left to stand at room temperature to isolate 79.7 g of a white primary crystal of 1-aminopyrrolidine hydrochloric acid salt, content: titrated 100.43%, GC98.40% (0.65 mole). Furthermore, the separated mother liquor was concentrated to give 21.9 g of a white secondary crystal of 1-aminopyrrolidine hydrochloric acid salt, content: titrated 97.03%, GC92.70% (0.17 mole). The yield of 1-amino-pyrrolidine hydrochloric acid salt crystal was 74.90%. The separated mother liquor contained 46.70% by weight [10.09 g (0.082 mole)] of 1-aminopyrrolidine hydrochloric acid salt remaining therein. The presence of a small amount of 1,4-butanediol was confirmed (GC analysis). The total yield of 1-aminopyrrolidine hydrochloric acid salt was 82.3%.

Example 3
Synthesis of 1-aminopyrrolidine hydrochloric acid salt:

A 1-liter glass autoclave was charged with 150.7 g (2.20 moles) of hydrazine monohydrochloride, 115.5 g (1.10 moles) of hyrazine dihydrochloride, 103.6 g (1.15 moles) of 1,4-butanediol and 401.3 g of $H_2O$. With stirring, these substances were reacted at 140° C. for 3.5 hours.

After the reaction, the reaction solution was concentrated under reduced pressure, and a mixture of (hydrazine monohydrochloride+hydrazine dihydrochloride) was washed with methanol to separate a white crystal in an amount of 181.2 g. The composititon of the mixture was titrated with 1N-NaOH to give 76.60% by weight [138.80 g (2.03 moles), the recovery rate 94.42%] of hyrazine monohychloride, 21.79% by weight [39.48 g (1.08 moles), the recovery rate 98.33%] of HCl.

The mixture of (hydrazine monohydrochloride+hydrazine dihydrocloride) was separated. The 1-aminopyrrolidine hydrochloric acid salt in 445.7 g of the methanol mother liquor had a content of 28.92% as titrated, 128.90 g (1.05 moles), and the formation rate was 91.42%. Incidentally, 1,4-butanediol did not remain (GC analysis).

The reaction selectivity was sought from the GC analysis of the methanol mother liquor. Four by-products existed in addition to 1-aminopyrrolidine. By a GC-MS analysis, one compound was determined to be hexahydropyridazine because it had a molecular weight of 86 and it had the same holding time (GC) as the standard sample. Another compound was determined to be tetrahydropyridazine because it had a molecular weight of 84, and it had the same holding time (GC) as a standard sample. Furthermore, the other two compounds were assumed to be 1,1-bipyrrolidine and octahydropyridazino[1,2-a]pyridazine because both had a molecular weight of 140. The reaction selectivities of the compounds in the methanol mother liquor were 90.17% of 1-aminopyrrolidine, 4.03% of hexahydropyridazine, 0.41% of tetrahydropyrazine, by-products having a molecular weight of 140, 4.72% of 1,1-bipyrrolidine, and 0.67% of octahydropyridazino[1,2-a]pyridazine, and the selective formation of 1-aminopyrrolidine was confirmed.

Example 4
Sythesis of 1-aminopyrrolidine hydrochloric acid salt:

A 1-liter glass autoclave was charged with 226.1 g (3.30 moles) of hydrazine monohydrochloride, 111.4 g (1.10 moles) of concentrated hydrochloric acid, 99.1 g (1.10 moles) of 1,4-butanediol and 330.0 g of $H_2O$. With stirring, these compounds were reacted at 130° C. for 5 hours.

After the reaction, the reaction solution was concentrated under reduced pressure, and a mixture of (hydrazine monohydrochloride+hydrazine dihydrochloride) was washed with methanol to sepatate 179.9 g of a white cyrstal. The composition of the mixture was determined by titration with 1N-NaOH and contained hydrazine monohydrochloride 86.54% by weight, [155.69 g (2.27 moles), the recovery rate 103.18%], and HCl 20.88% by weight, [37.57 g (1.03 moles), the recovery rate 93.57%].

128.1 g of the reaction concentrated methanol solution was allowed to stand at room temperature to isolate 66.8 g of a white primary crystal of 1-aminopyrrolidine hydrochloric acid salt. Content: titrated 99.40%, GC98.58% (0.54 mole). Furthermore, the separated mother liquor was concentrated to give 8.9 g of a white secondary crystal of 1-aminopyrrolidine hydrochloric acid salt, content: titrated 93.25%, GC94.36% (0.07 mole). The yield of 1-aminopyrrolidine hydrochloric acid salt crystal was 55.39%. The separated mother liquor contained 55.56% by weight of 1-aminopyrrolidine hydrochloric acid salt, 18.50 g (0.15 mole) remaining therein. Incidentally, a small amount of 1,4-butanediol was confirmed (GC analysis). The total yield of 1-aminopyrrolidine hydrochloride was 69.1%.

Example 5
Synthesis of 1-aminopyrrolidine hydrochloric acid salt:

A 1-liter glass autoclave was charged with 226.1 g (3.30 moles) of hydrazine monohydrochloride, 111.4 g (1.10 moles) of concentrated hydrochloric acid, 99.1 g (1.10 moles) of 1,4-butanediol, and 330.0 g of $H_2O$. With stirring, the above compounds were reacted at a temperature of 120° C. for 5 hours.

After the reaction, the reaction solution was concentrated under reduced pressure, and a mixture of (hydrazine monohydrochloride+hydrazine dihydrochloride) was washed with methanol to separate 205.0 g of a white crystal. The composition of the mixture was titrated with 1N-NaOH to give hydrazine monohydrochloride 80.28% by weight, 164.57 g (2.40 moles), the recovery rate 109.09%, and HCl 18.29% by weight, 37.49 g (1.03 moles), the recovery rate 93.38%.

A small amount of methanol was added to 107.6 g of the reaction concentrated solution, and the mixture was left to stand at room temperature to isolate 22.9 g of a white primary crystal of 1-aminopyrrolidine hydrochloric acid salt, content: titrated 99.73%, GC 99.13% (0.19 mole). Furthermore, the separated mother liquor was concentrated to obtain 36.5 g of a white secondary crystal of 1-aminopyrrolidine hydrochloric acid salt, content: titrated 93.56%, GC95.10% (0.28 mole). The yield of 1-aminopyrrolidine hydrochloric acid salt crystal was 42.30%. The separated mother liquor contained 58.91% by weight of 1-aminopyrrolidine hydrochloric acid salt [25.33 g (0.21 mole)] remaining therein. Incidentally, a small amount of 1,4-butanediol was confirmed (GC analysis). The total yield of 1-aminopyrrolidine hydrochloride salt was 61.0%.

Example 6
Precise distillation of 1-aminopyrrolidine

1-Aminopyrrolidine hydrochloric acid salt white crystal, Example 5, primary crystal 21.0 g (content: titrated 99.73%), secondary crystal 33.2 g (93.56%), Example 4, primary crystal 65.0 g (99.40%), secondary crystal 7.5 g (93.25%), Example 2, primary crystal 40.4 g (100.43%), and secondary crystal 20.5 g (97.03%) were dissolved in methanol, and the solution was neutralized with 60.0 g (1.50 moles) of NaOH. After neutralization, the precipitated sodium chloride was separated to give 207.2 g of a methanol solution of 1-aminopyrrolidine [1-aminopyrrolidine 44.80% by weight, 121.05 g (1.41 moles)].

A portion of this methanol solution was taken, and methanol was added to give 266.2 g (1.38 moles) of a methanol solution of 1-aminopyrrolidine. The above methanol solution was precisely distilled in a distillation tower filled with Helipack. After recovering methanol, 66.8 g (0.77 mole) of 1-aminopyrrolidine [content: 97.56% (GC)] was isolated at a boiling point of 128 to 130° C. The 1-aminopyrrolidine was identified with NMR.

$^1$H-NMR (CDCl$_3$); 1. 63–2.13 (m, 4H, —CH$_2$—); 2. 57–2.96 (m, 4H, —CH$_2$—); 3. 27 (bs, 3H, —NH$_2$),~D exchangeable

Example 7
Synthesis of 1-aminopyrrolidine hydrochloric acid salt

A 1-liter glass autoclave was charged with 274.0 g (4.00 moles) of hydrazine monohydrochloride, 105.5 g (1.00 mole) of hydrazine dihydrochloride, 90.1 g (1.00 mole) of 1,4-butanediol and 364.8 g of $H_2O$, and with stirring, these substances were reacted at 140° C. for 4 hours.

After the reaction, the reaction solution was concentrated under reduced pressure, and a mixture of (hydrazine monohydrochloride+hydrazine dihydrochloride) was washed with methanol to separate 301.8 g of a white crystal. The composition of the mixture was determined by titration with 1N-NaOH to give hydrazine monohydrochloride 86.26% by weight, 260.33 g (3.80 moles), the recovery rate 95.00% and HCl 10.95% by weight, 33.05 g (0.91 mole), the recovery rate 90.54%.

After separating the mixture of (hydrazine monohydrochloride+hydrazine dihydrochloride), 1-aminopyrrolidine hydrochloric acid salt in 310.8 g of the methanol mother liquor was 115.15 g (0.94 mole) [content: titrated 37.05%] and the formation rate was 93.92%.

The reaction selectivity in the methanol mother liquor was 91.89% of 1-aminopyrrolidine, 5.54% of hexahydropyridazine, a by-product having a molecular weight of 140, 2.28% of 1,1-bipyrrolidine and 0.29% of octahydropyridazino[1,2-a]pyridazine, and the selective formation of 1-aminopyrrolidine was confirmed. Incidentally, 1,4-butanediol did not remain (GC analysis).

Example 8
Synthesis of 1-aminopyrrolidine hydrochloric acid salt:

A 1-liter glass autoclave was charged with 75.4 g (1.10 moles) of hydrazine monohydrochloride, 115.5 g (1.10 moles) of hydrazine dihydrochloride, 99.1 g (1.10 moles) of 1,4-butanediol and 401.3 g of $H_2O$, and with stirring, the above compounds were reacted at 140° C. for 4 hours.

After the reaction, the reaction solution was concentrated under reduced pressure, and a mixture of (hydrazine monohydrochloride+hydrazine dihydrochloride) was washed with methanol to separate 122.0 g of a white crystal. The composition of the mixture was determined by titration with 1N-NaOH and contained, 68.09% by weight of hydrazine monohydrochloride [83.07 g (1.21 moles), the recovery rate 110.23%] and 30.69% by weight of HCl [37.44 g (1.03 moles), the recovery rate 93.25%].

After separating the mixture of (hydrazine monohydrochloride+hydrazine dihydrochloride), 1-aminopyrrolidine hydrochloric acid salt in 362.4 g of the methanol mother liquor contained 109.48 g (0.89 mole) [content: titrated 30.21%], and the formation rate was 80.91%.

The reaction selectivity in the methanol mother liquor was 88.30% of 1-aminopyrrolidine, 3.13% of hexahydropyridazine, a by-product having a molecular weight of 140, 6.40% of 1,1-bipyrrolidine and 0.83% of octahydropyridazino[1,2-a]pyridazine, and the selective formation of 1-aminopyrrolidine was confirmed. Incidentally, 1,4-butanediol remained in a small amount (GC analysis).

Example 9
Synthesis of 1-aminopyrrolidine hydrochloric acid salt:

A 1-liter glass autoclave was charged with 115.5 g (1.10 moles) of hydrazine dihydrochloride, 99.1 g (1.10 moles) of 1,4-butanediol and 401.3 g of $H_2O$, and with stirring, the above substances were reacted at 140° C. for 3.5 hours.

After the reaction, the reaction solution was concentrated under reduced pressure, and a mixture of (hydrazine monohydrochloride+hydrazine dihydrochloride) was washed with methanol to separate 54.9 g of a white crystal. The composition of the mixture was titrated with 1N-NaOH was as follows: hydrazine monohydrochloride 64.21% by weight, 35.25 g (0.51 mole), HCl 33.99% by weight, 18.66 g (0.51 mole).

After separating the mixture of (hydrazine monohydrochloride+hydrazine dihydrochloride), 1-aminopyrrolidine hydrochloric acid salt in 475.2 g of the methanol mother liquor was as follows: content: titrated 13.36%, 63.49 g (0.52 mole), and the formation rate 47.07%.

17

The reaction selectivity in the methanol mother liquor was 81.22% of 1-aminopyrrolidine, 2.34% of hexahydropyridazine, a by-product having a molecular weight of 140, 8.12% of 1,1-bipyrrolidine, and 0.89% of octahydropyridazino[1,2-a]pyridazine. Incidentally, 1,4-butanediol remained in a small amount (GC analysis).

Example 10
Synthesis of 1-aminopyrrolidine hydrochloric acid salt by tetrahydrofuran A 1-liter glass autoclave was charged with 150.7 g (2.20 moles) of hydrazine monohydrochloride, 115.5 g (1.10 moles) of hydrazine dihydrochloride, 79.3 g (1.10 moles) of tetrahydrofuran and 401.3 g of $H_2O$, and with stirring, the above substances were reacted at 140° C. for 3.5 hours.

After the reaction, the reaction solution was concentrated under reduced pressure, and a mixture of (hydrazine monohydrochloride+hydrazine dihydrochloride) was washed with methanol to separate 187.6 g of a white crystal. The composition of the mixture was determined by titration with 1N-NaOH with the following results. Hydrazine monohydrochloride 77.90% by weight, 146.14 g (2.13 moles), the recovery rate 96.96%, HCl 20.05% by weight, 37.61 g (1.03 moles), and the recovery rate 93.68%.

The reaction concentrated solution (152.8 g) was allowed to stand to isolate 79.1 g of a white primary crystal of 1-aminopyrrolidine hydrochloric acid salt [content:titrated 99.71% (0.65 mole)]. Furthermore, the separated mother liquor was concentrated to give 22.3 g of a white secondary crystal of 1-aminopyrrolidine hydrochloric acid salt, content:titrated 94.79% (0.18 mole). The yield of 1-aminopyrrolidine hydrochloric acid salt crystal was 75.45%. In the separated mother liquor, 74.20% by weight [17.07 g (0.14 mole)] of 1-aminopyrrolidine hydrochloric acid salt remained. The total yield of 1-aminopyrrolidine was 88.2%.

Example 11
Synthesis of 1-aminopyrrolidine hydrobromic acid salt

A 200 ml pressure-resistant glass bomb was charged with 101.7 g (0.45 mole) of 50% hydrazine hyrobromide, 25.8 g (0.45 mole) of 47% hydrobromic acid, and 13.5 g (0.15 mole) of 1,4-butanediol, and the above substances were reacted at 140° C. for 3.5 hours.

After the reaction, the formation rate of 1-aminopyrrolidine hydrobromide during the reaction was 88.4% (quantitatively analyzed by GC).

The selectivity in the reaction solution was 73.61% of 1-aminopyrrolidine hydrobromic acid salt, 5.66% of hexahydropyridazine, a by-product having a molecular weight of 140, 16.13% of 1,1-bipyrrolidine, and 3.50% of octahydropyridazino [1,2-a]pyridazine. Incidentally, 1,4-butanediol did not remain (GC analysis).

Example 12
Precise distillation of 1-aminopyrrolidine

After synthesizing 1-aminopyrrolidine hydrochloric acid salt, 656.5 g of a 1-aminopyrrolidine hydrochloric acid salt reaction solution [Composition: (1-aminopyrrolidine hydrochloric acid salt+hydrazine monohydrochloride) 83.05% by weight, 545.22 g (4.45 moles), HCl 2.40% by weight, 15.76 g (0.43 mole)] remaining after recovering a mixture of (hydrazine monohydrochloride+hydrazine dihydrochloride) was formed. To the above 1-aminopyrrolidine hydrochloric acid salt solution was added 100 g of methanol, and the methanol solution was neutralized with 200.1 g (5.00 moles) of sodium hydroxide. After neutralization, 330.2 g of sodium chloride was separated. Thereafter, 969.6 g of

18

1-aminopyrrolidine methanol solution [composition: 1-aminopyrrolidine 29.43% by weight, 285.35 g (3.31 moles), hydrazine hydrate 4.90% by weight, 47.56 g (0.95 mole)] was obtained. 912.1 g of 1-aminopyrrolidine methanol neutralized solution [composition: 1-aminopyrrolidine 29.43% by weight, 268.4 g (3.12 moles), hydrazine hydrate 4.90% by weight, 45.1 g (0.90 mole), methanol 57.78% by weight, 527.0 g, $H_2O$ 7.86% by weight, 71.7 g] was precisely distilled by using a distillation tower packed with Helipack. After recovering methanol at normal pressure, methanol, water, hydrazine hydrate, and pyrrolidine fractions were removed under reduced pressure, and 99.3% (GC) of 1-aminopyrrolidine was isolated at 70 mmHg and 55 to 62° C.

Example 13
Synthesis of 1-aminopiperidine hydrochloric acid salt

A 200 ml pressure-resistant glass bomb was charged with 27.4 g (0.40 mole) of hydrazine monohydrochloride, 21.0 g (0.20 mole) of hydrazine dihydrochloride, 20.8 g (0.20 mole) of 1,5-pentanediol and 60.0 g of $H_2O$, and by a shaking machine, the above substances were reacted at 140° C. for 24 hours.

After the reaction, the reaction solution was separated into two layers. After separation, the upper layer and the lower layer were separately treated.

By a GC-MS analysis of the upper layer reaction solution, the formation of 5-chloro-l-pentanol as a chlorinated product of 1,5-pentanediol, and 1,5-dichloropentane was ascertained.

The lower layer reaction solution was concentrated under reduced pressure, and a mixture of (hydrazine monohydrochloride+hydrazine dihydrochloride) was washed with methanol to separate 34.4 g of a white crystal. The composition of the mixture was titrated with 1N-NaOH to give hydrazine monohydrochloride 84.24% by weight, 28.98 g (0.42 mole), the recovery rate 105.75% and HCl 13.15% by weight, 4.52 g (0.12 mole), the recovery rate 62.0%.

The mixture of (hydrazine monohydrochloride+hydrazine dihydrochloride) was separated, and 1-aminopiperidine hydrochloric acid salt in 97.3 g of the methanol mother liquor was 14.93% (titrated), 14.53 g (0.11 mole), and the formation rate was 53.2%. 1-Aminopiperidine was identified by GC-MS and the fact that the holding time of GC of the standard sample coincided with the holding time of GC of the product. Incidentally, the reaction selectivity of 1-aminopiperidine was 92.9% (GC).

Example 14
Synthesis of 1-aminopiperidine hydrochloric acid salt

A 200 ml pressure-resistant glass bomb was charged with 27.4 g (0.40 mole) of hydrazine monohydrochloride, 21.0 g (0.20 mole) of hyrazine dihydrochloride, 17.2 g (0.20 mole) of tetrahydropyran and 60.0 g of $H_2O$, and by a shaking machine, the above substances were reacted at 140° C. for 24 hours.

After the reaction, the reaction solution was separated into two layers. After separating the solution, the upper layer and the lower layer were separately treated.

In the upper layer, the formation of 5-chloro-1-pentanol which was a chlorinated product of 1,5-pentanediol, and 1,5-dichloropentane was confirmed.

The lower layer reaction solution was concentrated under reduced pressure, and a mixture of (hydrazine monohydrochloride+hydrazine dihydrochloride) was recovered to obtain 89.5 g of the reaction concentrated methanol mother liquor. 1-Aminopiperidine hydrochloric acid salt in the methanol mother liquor was 2.75% as titrated [2.46 g (0.07 mole)], the formation rate 33.8%].

Example 15
Synthesis of 1-amino-4-methylpiperidine hydrochloric acid salt

A 1-liter glass autoclave was charged with 226.1 g (3.30 moles) of hydrazine monohydrochloride, 111.4 g (1.10 moles) of concentrated hydrochloric acid, 127.8 g (1.10 moles) of 3-methyl-1,5-pentanediol and 400.0 g of $H_2O$, and with stirring, the above substances were reacted at 140° C. for 24 hours.

After the reaction, the reaction solution was separated into two layers. Then, after separation, the upper layer and the lower layer were separately treated.

By a GC-MS analysis of the upper layer reaction solution, the formation of 5-chloro-3-methyl-1-pentanol which was a chlorinated product of 3-methyl-1,5-pentanediol and 1,5-dichloro-3-methylpentane was confirmed.

The lower layer reaction solution was concentrated under reduced pressure, and a mixture of (hydrazine monohydrochloride+hydrazine dihydrochloride) was recovered to give 174.4 g of the reaction concentrated methanol mother liquor. 1-Amino-4-methylpiperidine hydrochloric acid salt in the methanol mother liquor was 8.57% as titrated, 15.20 g (0.10 mole), and the formation rate was 9.2%. Incidentally, 1-amino-4-methylpiperidine was identified by GC-MS.

Example 16
Synthesis of 1-aminohexamethyleneimine hydrochloric acid salt

A 1-liter glass autoclave was charged with 150.7 g (2.20 moles) of hydrazine monohydrochloride, 115.5 g (1.10 moles) of hydrazine dihydrochloride, 130.0 g (1.10 moles) of 1,6-hexanediol and 401.3 g of $H_2O$, and with stirring, the above substances were reacted at 140° C. for 22 hours.

After the reaction, the reaction solution was separated into two layers. Then, after the separation, the upper layer and the lower layer were separately treated.

By the GC-MS analysis of the upper layer reaction solution, the formation of 6-chloro-1-hexanol which was a chlorinated product of 1,6-hexanediol, and 1,6-dichlorohexane was confirmed.

The lower layer reaction solution was concentrated under reduced pressure, and a mixture of (hydrazine monohydrochloride+hydrazine dihydrochloride) was washed with methanol to separate 134.7 g of a white crystal. The composition of the mixture was determined by titration with 1N-NaOH to give 79.37% by weight of hydrazine monohydrochloride [106.9 g (1.56 moles), the recovery rate 70.95%], and 18.37% by weight of HCl [24.7 g (0.68 mole), the recovery rate 61.6%].

After separating the mixture of (hydrazine monohydrochloride+hydrazine dihydrochloride), the amount of 1-aminohexamethyleneimine hydrochloric acid salt in the methanol mother liquor was 6.26 g (0.055 mole), and the formation rate was 4.98%. 1-Aminohexamethyleneimine was identified by GC-MS and the fact that the holding time of GC of the standard sample coincided with the holding time of GC of the product.

Example 17
Synthesis of pyrazolidine hydrochloric acid salt

A 1-liter glass autoclave was charged with 226.1 g (3.30 moles) of hydrazine monohydrochloride, 111.4 g (1.10 moles) of concentrated hydrochloric acid, 83.7 g (1.10 moles) of 1,3-propanediol and 400.0 g of $H_2O$, and with stirring, the above substances were reacted at 140° C. for 5 hours.

After the reaction, the reaction solution was concentrated under reduced pressure, and a mixture of (hydrazine monohydrochloride+hydrazine dihydrochloride was washed with methanol to recover a white crystal.

After separating the mixture of (hydrazine monohydrochloride+hydrazine dihydrochloride), pyrazolidine hydrochloride in 393.1 g of the methanol mother liquor had a content of 20.16% (titrated), 79.25 g (0.73 mole), the formation rate 66.4%. Furthermore, the formation of tetrahydro-1H, 5H-pyrazolo-[1,2-a]pyrazole as a by-product was confirmed. Pyrazolidine and tetrahydro-1H, 5H-pyrozolo-[1,2-a] pyrazole were identified by GC-MS. The reaction selectivity was 79.01% of pyrazolidine and 17.76% of tetrahydro-1H, 5H-pyrazolo-[1,2-a]pyrazole, and 3.23% of 1, 3-propanediol remained (GC).

In the presence of an inorganic acid, 1,4-butanediol was reacted with hydrazine hydrohalogenic acid salt to give 1-aminopyrrolidine. Accordingly, if the same reaction proceeded in the case of 1,3-propanediol, trimethyleneimine would be presumably formed. But it could not be confirmed by a GC-MS analysis. The product was pyrazolidine in which two nitrogens of hydrazine are incorporated in a 5-membered ring. The cause of this case is ascribable to the magnitude of a distortion energy of trimethyleneimine (formula 16).

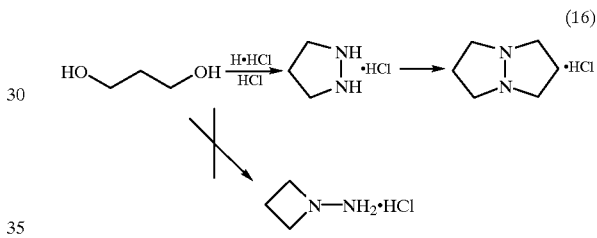

(16)

Example 18
Synthesis of pyrazolidine hydrochloric acid salt

A 1-liter glass autoclave was charged with 75.4 g (1.10 moles) of hydrazine monohydrochloride, 230.9 g (2.20 moles) of hydrazine dihydrochloride, 83.7 g (1.10 moles) of 1,3-propanediol and 400.0 g of $H_2O$, and with stirring, the above substances were reacted at 140° C. for 5 hours.

After the reaction, the reaction solution was concentrated under reduced pressure, and a mixture of (hydrazine monohydrochloride+hydrazine dihydrochloride) was washed with methanol to separate 233.8 g of a white crystal. The composition of the mixture was determined by titration with 1N-NaOH to give hydrazine monohydrochloride 65.24% by weight, [152.53 g (2.23 moles), the recovery rate 101.23%] and HCl 31.67% by weight, [74.04 g (2.03 moles), the recovery rate 92.23%].

After separating the mixture of (hydrazine monohydrochloride+hydrazine dihydrochloride), pyrazolidine hydrochloride in 109.6 g of the methanol mother liquor was 61.26% (titrated), 67.14 g (0.62 mole), and the formation rate was 56.2%. The reaction selectivity was 75.69% of pyrazolidine and 24.31% of tetrahydro-1H, 5H-pyrazolo-[1, 2-a]pyrazole. Incidentally, 1,3-propanediol did not remain (GC).

Example 19
Synthesis of pyrazolidine hydrochloride acid salt

A 1-liter glass autoclave was charged with 150.7 g (2.20 moles) of hydrazine monohydrochloride, 115.5 g (1.10 moles) of hydrazine dihydrochloride, 83.7 g (1.10 moles) of 1,3-propanediol and 400.0 g of $H_2O$, and with stirring, the above substances were reacted at 140° C. for 5 hours.

After the reaction, the reaction solution was concentrated under reduced pressure, and a mixture of (hydrazine monohydrochloride+hydrazine dihydrochloride) was washed with methanol to separate 201.2 g of a white crystal. The composition of the mixture was determined by titration with 1N-NaOH to give 80.89% by weight of hydrazine monohydrochloride [162.75 g (2.38 moles), the recovery rate 108.00%], and 17.55% by weight of HCl, [35.30 g (0.97 mole), the recovery rate 87.91%].

After separating the mixture of (hydrazine monohydrochloride+hydrazine dihydrochloride), pyrazolidine hydrochloride in 109.7 g of the methanol mother liquor was 57.64% (titrated), 63.23 g (0.58 mole), and the formation rate was 52.9%. The reaction selectivity was 77.22% of pyrazolidine and 20.81% of tetrahydro-1H, 5H-pyrazolo-[1,2-a]pyrazole. It was found that 1.97% of 1,3-propanediol remained (GC).

Example 20
Synthesis of 4-aminomorpholine hydrochloric acid salt

A 1-liter glass autoclave was charged with 150.2 g (3.00 moles) of hydrazine hydrate, 405.1 g (4.00 moles) of concentrated hydrochloric acid, and 106.1 g (1.00 mole) of diethylene glycol, and with stirring, the above substances were reacted at 140° C. for 10 hours.

After the reaction, the reaction solution was concentrated under reduced pressure, and a mixture of (hydrazine monohydrochloride+hydrazine dihydrochloride) was washed with methanol to separate 144.4 g of a white crystal. The composition of the mixture was titrated with 1N-NaOH to give hydrazine monohydrochloride 87.72% by weight, 119.45 g (1.74 moles), the recovery rate 87.18%, HCl 16.09% by weight, 23.23 g (0.64 mole), the recovery rate 63.65%.

After separating the mixture of (hydrazine monohydrochloride+hydrazine dihydrochloride), a suitable amount of methanol was added to 133.2 g of the methanol mother liquor, and the hydrochloric acid content in the methanol mother liquor was neutralized with 35.5 g (0.89 mole) of sodium hydroxide. 4-Aminomorpholine in the methanol mother liquor was 4.47 g (0.044 mole), the formation rate 4.37%, diethylene glycol 67.7 g (0.638 mole), the conversion 36.2%. 4-Aminomorpholine and diethylene glycol were identified by GC-MS and the fact that the holding time of GC of the standard sample coincided with a holding time of GC of the product.

Example 21
Sythesis of tetrahydropyridazine

1-Aminopyrrolidine [18.95 g (0.22 mole)] was dissolved in 50 g of methanol, and air in an amount of about 10 times the theoretical amount was blown in the 1-aminopyrrolidine methanol solution at 40° C. for 40 hours to perform an oxidation reaction. After the reaction, the composition of the reaction solution was analyzed by GC to find that it contained 12.38% of pyrrolidine, 4.61% of 1-aminopyrrolidine, 2.07% of hexahydropyridazine and 74.06% of tetrahydropyridazine (area percent). The remaining 1-aminopyrrolidine in the oxidation reaction solution was quantitatively analyzed to seek the conversion of 1-aminopyrridazine. Since the remaining 1-aminopyrrolidine was 0.5865 g (0.0068 mole) in the oxidation reaction solution, the conversion of 1-aminopyrrolidine was 96.9%.

Example 22
Synthesis of tetrahydropyridazine

1-Aminopyrrolidine hydrochloric acid salt [18.95 g (0.22 mole)] was dissolved in methanol, and the methanol solution was nuetralized with 8.0 g (0.20 mole) of sodium hydroxide. Sodium chloride was filtered and separated, and the amount of the separated 1-aminopyrrolidine methanol solution was 129.6 g. Air in an amount of about 3.3 times the theoretical amount was blown into the 1-aminopyrrolidine methanol solution under refluxing by heating for 22 hours to carry out an oxidation reaction. After the reaction, the composition of the reaction solution was analyzed by GC and was found to contain 1.93% of pyrrolidine, 10.45% of 1-aminopyrrolidine, 6.54% of hexahyropyridazine and 79.18% of tetrahyrdopyridazine (area percent). From 1.5009 g (0.0174 mole) of the remaining 1-aminopyrrolidine in the oxidation reaction solution, the conversion of 1-aminopyrrolidine was 92.1%.

Example 23
Distillation of tetrahydropyridazine

A tetrahydropyridazine oxidation reaction solution containing 13.7% by weight of tetrahydropyridazine [31.0 g (0.369 mole)] was precisely distilled using a distillation tower packed with Helipack. At 10 mmHg and 47–53° C., 16.4 g of a distillation fraction was isolated. The composition of the fraction consisted of 92.0% of tetrahydropyridazine, 1.1% of pyrrolizine, 3.2% of 1-aminopyrrolidine and 0.5% of hexahydropyridazine (GC area percent). Incidentally, the structure of tetrahydropyridazine was ascertained by NMR.

$^1$H-NMR (CDCl$_3$); 1.67–2.47 (m, 4H, —CH$_2$—); 3.01–3.30 (m, 4H, —CH$_2$—); 5.57 (bs, 1H, —NH—)~D exchangeable 6.99 (s, 1H, =CH—)

Example 24
Synthesis of tetrahydropyridazine

Methanol (50 g) was added to 1028.5 g of a 1-aminopyrrolidine hydrochloric acid salt solution containing the reaction solution synthesized by using hydrazine hydrochloric acid salt, and the methanol solution was neutralized with 140.0 g (3.50 moles) of sodium hydroxide. Sodium chloride in the neutralized methanol solution was filtered and separated. The amount of sodium chloride was 183.8 g.

Into the neutralized 1-aminopyrrolidine solution (1633.5 g) obtained by adding the washing liquor [composition: 1-aminopyrrolidine 13.67% by weight, 223.25 g (2.592 moles), hydrazine hydrate 1.82% by weight, 29.69 g (0.593 mole), methanol 80.16% by weight, 1309.38 g (40.867 moles), H$_2$O 3.82% by weight, 62.33 g (3.459 moles), sodium hydroxide 1.20% by weight, 19.53 g (0.488 mole)], air was blown at a rate of 1.5 liters/min. and an oxidation reaction was carried out at 63 to 65° C. for 28 hours.

After the reaction, hydrazine hydrate did not remain in the tetrahydropyridazine methanol solution. This was because hydrazine hydrate was decomposed during the oxidation reaction. The oxidation reaction solution contained 1.88% of pyrrolidine, 8.53% of 1-aminopyrrolidine, 5.74% of hexahydropyridazine and 76.33% of tetrahydropyridazine (GC area percent). By a one-point calibration curve method, 1-aminopyrrolidine and tetrahydropyridazine were quantitatively analyzed. From 0.74% by weight, 12.09 g (0.140 mole) of 1-aminopyrrolidine, tetrahydropyridazine in the oxidation reaction solution was 12.63% by weight, 206.26 g (2.452 moles), yield 94.6%.

After the oxidation reaction, from 1632.6 g of the reaction solution, methanol was recovered at normal pressure by using a distillation tower packed with Helipack, and the reaction solution was precisely distilled under reduced pressure. At 54 to 55° C. and 10 mmHg, 97% of tetrahydropyridazine was isolated. The distillation yield was 48.9%.

Example 25

Synthesis of tetrahydropyridazine

To 1231.6 g of a 1-aminopyrrolidine hydrochloride solution containing a reaction solution synthesized by using hydrazine hydrochloride, 184.7 g (4.617 moles) of sodium hydroxide (equimolar amount) was added, and the solution was neutralized at 30 to 40° C. Sodium chloride in the neutralized methanol solution was filtered and separated, and thereafter, sodium chloride was washed fully with methanol. The amount of sodium chloride was 249.7 g.

Into 1226.0 g of a neutralized methanol solution obtained by adding the washing liquor [composition: 1-aminopyrrolidine 23.26% by weight, 285.17 g (3.311 moles), hydrazine hydrate 4.32% by weight, 52.91 g (1.057 moles)] air was blown at a rate of 1.5 liters/min., and an oxidation reaction was carried out at 65 to 75° C. under reflux with heating for 104 hours.

The composition of the oxidation reaction solution contained 7.07% of pyrrolidine, 4.22% of 1-aminopyrrolidine, 0.13% of hexahyropyridazine and 87.28% of tetrahydropyridazine. Hydrazine hydrate existed at the time of beginning the oxidation reaction was decomposed, and was not recognized in the reaction solution (GC). In comparison with Example 24, since excessive sodium hydroxide did not exist after the neutralization, the reaction speed was slow, and the the formed amount of pyrrolidine which was the decomposition product of 1-aminopyrrolidine increased. In the oxidation reaction of 1-aminopyrrolidine, it was found that the presence of alkali increased the speed of the reaction.

A suitable amount of methanol was added to 730.1 g of the tetrahydropyridazine, and the resulting solution was simply distilled under reduced pressure at a distilltion temperature: room temperature to 90° C. and 23 mmHg, and a mixture of pyrrolidine, 1-aminopyrrolidine and tetrahydropyridazine was separated as a fraction.

The yield of the oxidation reaction from 1-aminopyrrolidine to tetrahydropyridazine was 87.1%, and the yield of distillation was 67.3%. Furthermore, the reaction selectivity was 87.10% of tetrahydropyridazine, 2.93% of 1-aminopyrrolidine and 4.02% of pyrrolidine.

TABLE 1

|  | g | APD | Pyrrolidine | THP | Total |
| --- | --- | --- | --- | --- | --- |
| materials charged for distillation | 861.2 | 0.097 (mol) | 0.133 (mol) | 2.884 (mol) | 3.114 (mol) |
| Fraction 1 | 555.0 | 0.088 | 0.131 | 1.568 | 1.787 |
| Fraction 2 | 181.7 | 0.003 | 0.002 | 0.373 | 0.378 |
| Can residue | 124.5 | 0.006 | trace | 0.943 | 0.949 |
| Fractions + can residue | 861.2 | 0.097 | 0.133 | 2.884 | 3.114 |

APD = 1-aminopyrrolizine, THP = tetrahydropyridazine

Example 26

Synthesis of tetrahydropyridazine

To 1050.7 g of a 1-aminopyrrolidine hydrochloric acid salt solution containing a reaction solution synthesized by using hydrazine hydrochloric acid salt was added 181.7 g (4.542 moles) of sodium hydroxide (1.05 equivalents), and the solution was neutralized at 30 to 40° C. Sodium chloride in the neutralized methanol solution was filtered and separated, and then the residue was fully washed with methanol. The amount of sodium chloride was 241.2 g (4.127 moles), the recovery rate 95.4%.

Into 1007.1 g of the neutralized methanol solution obtained by adding the washing liquor [composition: 1-aminopyrrolidine 27.13% by weight, 273.23 g (3.172 moles), hydrazine hydrate 5.02% by weight, 50.06 g (1.000 mole)], while blowing air at a rate of 3.0 liters/min., an oxidation reaction was carried out at 65 to 75° C. for 74 hours under reflux with heating. In 35 hours after the beginning of the reaction, the speed of the reaction was decreased. Therefore, 0.05 equivalent of sodium hydroxide was added, and the reaction was resumed. By adding sodium hydroxide, the speed of the reaction again increased, and the decomposition side reaction to pyrrolidine was suppressed. The increase of the speed of the oxidation reaction of 1-aminopyrrolidine requires the presence of an inorganic base.

After the end of the reaction, the oxidation reaction solution was analyzed by GC. As a result, the selectivity was pyrrolidine 2.55%, tetrahydropyridazine 91.46%, and 1-aminopyrrolidine 0.81%. Hydrazine hydrate existing at the beginning of the oxidation reaction was decomposed, and was not recognized in the reaction solution.

Example 27

Synthesis of tetrahydropyridazine

A 20% aqueous solution of 1-aminopyrrolidine in an amount of 50.0 g (0.116 mole) was heated to 90° C., and while the reaction temperature was maintained at 90° C., 43.43 g (0.128 mole) of 10% aqueous hydrogen peroxide was added over 5 hours [charged mole ratio: aqueous hydrogen peroxide/1-aminopyrrolidine=1.1]. After the addition, the solution was stirred at 90° C. for 1 hour, and cooled to room temperature. Then, the oxidation reaction solution (93.6 g) was quantitatively analyzed (GC).

Tetrahydropyridazine 6.82% by weight, 6.38 g (0.076 mole), 1-aminopyrrolidine 0.69% by weight, 0.65 g (0.008 mole), the yield of tetrahydropyridazine 65.3%, the conversion of 1-aminopyrrolidine 93.5%.

Example 28

Synthesis of tetrahydropyridazine

A 20% aqueous solution of 1-aminopyrrolidine in an amount of 50.0 g (0.116 mole) was heated to 70° C., and while the reaction temperature was maintained at 70° C., a 3% aqueous hydrogen peroxide in an amount of 158.3 g (0.142 mole) [charge mole ratio: aqueous hydrogen peroxide/1-aminopyrrolidine=1.2] was added over 10 hours. After the addition, the solution was stirred at 70° C. for 1 hour, and cooled to room temperature, and the oxidation reaction solution (207.2 g) was quantitatively analyzed (GC).

Tetrahydropyridazine 2.75% by weight, 5.70 g (0.068 mole), 1-aminopyrrolidine 0.08% by weight, 0.17 g (0.002 mole), the yield of tetrahydropyridazine 58.4%, the conversion of 1-aminopyrrolidine 98.3%.

Example 29

Synthesis of tetrahydropyridazine

A 20% aqueous solution of 1-aminopyrrolidine [50.0 g (0.116 mole)] was heated to 70° C., and while the reaction temperature was maintained at 70° C., a 10% aqueous solution of hydrogen peroxide [39.5 g (0.116 mole)] [charged mole ratio: aqueous hydrogen peroxide/l-aminopyrrolidine=1.0] was added over 5 hours. After the addition, the solution was stirred at 70° C. for 1 hour, cooled to room temperature, and the oxidation reaction solution (89.2 g) was quantitatively analyzed (GC).

Tetrahydropyridazine 6.65% by weight, 5.93 g (0.071 mole), 1-aminopyrrolidine 1.45% by weight, 1.29 g (0.015 mole), the yield of tetrahydropyridazine 60.8%, the conversion of 1-aminopyridazine 87.1%.

Example 30
Synthesis of tetrahydropyridazine

A 20% aqueous solution of 1-aminopyrrolidine [50.0 g 0.116 mole)] was heated to 50° C., and while the reaction temperature was maintained at 50° C., 158.0 g (0.140 mole) of a 3% aqueous solution of hydrogen peroxide [charged mole ratio: aqueous hydrogen peroxide/1-aminopyrrolidine=1.2] was added over 2.5 hours. After the addition, the solution was stirred at 50° C. for 1 hour, cooled to room temperature, and the oxidation reaction solution 207.1 g was quantitatively analyzed (GC).

Tetrahydropyridazine 2.29% by weight, 4.73 g (0.056 mole), 1-aminopyrrolidine 0.21% by weight, 0.43 g (0.005 mole), the yield of tetrahydropyridazine 48.3%, the conversion of 1-aminopyrrolidine 95.7%.

Example 31
Synthesis of tetrahydropyridazine

To 50.0 g (0.116 mole) of a 20% aqueous solution of 1-aminopyrrolidine, 157.9 g (0.139 mole) of a 3% aqueous solution of hydrogen peroxide was added at room temperature over 2 hours [charge mole ratio: aqueous hydrogen peroxide/1-aminopyrrolidine=1.2]. After the addition, the solution was stirred at room temperature for 1 hour, cooled to room temperature, and the oxidation reaction solution (207.1 g) was quantitatively analyzed (GC).

Tetrahydropyridazine 1.89% by weight, 3.91 g (0.046 mole), 1-aminopyrrolidine 0.24% by weight, 0.50 g (0.006 mole), the yield of tetrahydropyridazine 40.0%, the conversion of 1-aminopyrrolidine 95.0%.

Example 32
Synthesis of tetrahydropyridazine

1-Aminopyrrolidine hydrochloric acid salt obtained by reacting hydrazine hydrate, concentrated hydrochloric acid, and 1,4-butanediol was neutralized with sodium hydroxide. Thereafter, 1000.0 g of a 1-aminopyrrolidine aqueous solution fraction obtained by simple distillation [the composition of simple distillation fraction of the 1-aminopyrrolidine aqueous solution: 1-aminopyrrolidine 15.07% by weight, 150.71 g (1.750 moles), hydrazine hydrate 0.89% by weight, 8.90 g (0.178 mole), octahydropyridazino[1,2-a]pyridazine 1.08% by weight, 10.79 g (0.077 mole), 1,1-bipyrrolidine 3.26% by weight, 32.60 g (0.232 mole)] was heated to 90° C., and while the reaction temperature was maintained at 90° C., 257.1 g (2.630 moles) of a 30% aqueous solution of hydrogen peroxide [charged mole ratio: aqueous hydrogen peroxide/1-aminopyrrolidine=1.3, aqueous hydrogen peroxide/hydrazine hydrate=2.0] was added dropwise over 5 hours. After the addition, the solution was stirred at 90° C. for an hour, cooled to room temperature, and the oxidation reaction solution (1252.3 g) was quantitatively analyzed (GC).

Tetrahydropyrydazine 7.03% by weight, 88.03 g (1.047 moles), 1-aminopyrrolizine 1.13% by weight, 14.11 g (0.164 mole), the yield of tetrarhydropyridazine 59.8%, and the conversion of 1-aminopyrrolidine 90.6%. Incidentally, most of hydrazine hydrate, octahydropyridazino[1,2-a]pyridazine and 1,1-bipyrrolidine contained in the 1-aminopyrrolidine aqueous solution fraction were decomposed during the 1-aminopyrolidine oxidation reaction. By GC analysis of the oxidation reaction solution, they were below the detection limit.

Example 33
Synthesis and separation of 1-aminopyrrolidine

A 50-liters glass reactor was charged with 5.006 Kg (100.0 moles) of hydrazine hydrate, 20.256 Kg (200.0 moles) of 36% HCl and 9.012 Kg (100.0 moles) of 1,4-butanediol [total charged amounts 34.28 Kg], and the above substances were reacted at a reaction temperature of 120 to 140° C. for 4.5 hours, and further reacted at 140° C. for 2 hours. The maximum pressure during the reaction was 3 Kg/cm$^2$G. After the reaction, the reaction mixture was cooled to room temperature, and neutralized with 16.70 kg (200.0 moles) of 48% NaOH aqueous solution to give 50.93 Kg of 1-aminopyrrolidine neutralized reaction solution. The composition of the 1-aminopyrrolidine neutralized reaction solution was 1-aminopyrrolidine 10.26% by weight, 5.225 Kg (60.7 moles), hydrazine hydrate 3.05% by weight, 1.553 Kg (31.0 moles), octahydropyridazino[1,2-a]pyridazine 0.44% by weight, 0.224 Kg (1.6 moles), 1,1-bipyrrolidine 1.94% by weight, 0.988 Kg (7.0 moles), the yield of 1-aminopyrrolidine (based on 1,4-butanediol) 60.7%.

The neutralized reaction solution was subjected to simple distillation whereby about 50% of the charged neutralized reaction solution taken at a bottom temperature of 101 to 113° C. and at a top temperature of 69 to 100° C. was separated as fraction-(1) 25.65 Kg. To a can residual solution-1 from which the fraction-(1) was separated, 5.25 Kg of H$_2$O (which was about 10% of the charged neutralized reaction solution) was added, and again, the solution was subjected to simple distillation. At a bottom temperature of 112 to 114° C. and a top temperature of 95 to 100° C., a fraction-(2) 5.25 Kg, an equal weight of the amount added of water, were separated. The composition of simple distillation fractions-(1+2) 30.90 Kg contained 1-aminopyrrolidine 14.00% by weight, 4.326 Kg (50.2 moles), the recovery rate in simple distillation 82.74%, hyrazine hydrate 0.51% by weight, 0.158 Kg (3.1 moles), the recovery rate in simple distillation 10.15%, octahydropyridazino[1,2-a]pyridazine 0.72% by weight, 0.222 Kg (1.6 moles), 1,1-bipyrrolidine 3.40% by weight, 1.051 Kg (7.5 moles).

Example 34
Synthesis of tetrahydropyridazine

Simple distillation fraction-(1+2) obtained in Example 33 (30.85 Kg) [composition: 1-aminopyrrolidine 14.00% by weight, 4.319 Kg (50.1 moles), hydrazine hydrate 0.51% by weight, 0.157 Kg (3.1 moles)] was heated to 90° C., and 7.00 Kg (71.4 moles) of a 34.70% aqueous solution of hydrogen peroxide [the charged mole ratio: aqueous hydrogen peroxide (mole)=1-aminopyrrolidine×1.3+hydrazine hydrate× 2.0] was added dropwise over a period of 2 hours and 15 minutes while maintaining a reaction temperature at 90 to 95° C. Furthermore, the reaction solution was stirred at 90° C. for 2 hours and cooled. When the oxidation reaction solution was analyzed, the amount of tetrahydropyridazine was 6.43%, but the 1-aminoprrolidine remained in an amount of 1.99%. Then, at a reaction temperature of 90° C., 0.90 Kg (9.1 moles) of a 34.70% aqueous solution of hydrogen peroxide was added dropwise for 15 minutes [the total charged mole ratio: aqueous hydrogenperoxide/1-aminopyrrolidine=1.48]. After adding hydrogen peroxide dropwise, the mixture was stirred for 30 minutes at 90° C., and cooled to room temperature, and the oxidation reaction solution was analyzed. Tetrahydropyridazine 6.45%, and 1-aminopyrrolidine 1.10%. To the oxidation reaction solution was added 18.50 Kg (462.5 moles) of flaky sodium hydroxide, and the solution was stirred, dissolved and left to stand and separated into the tetrahydropyridazine layer and the water layer. The amount of sodium hydroxide added was adjusted so that the water layer after liquid separation became about 35% aqeuous solution of sodium hydroxide. After liquid separation, the tetrahydropyridazine layer and the water layer were respectively analyzed. The results were as follows: (The upper layer) tetrahydropyridazine layer 6.35 Kg {composition: tetrahydropyridazine 39.25% by weight, 2.492 Kg (29.6 moles), 1-aminopyrrolidine 6.46% by weight, 0.410 Kg (4.8 moles), octahydropyridazino[1,2-a]pyridazine 0.29% by weight, 0.018 Kg (0.1 mole), 1,1-bipyrrolidine 0.51% by weight, 0.032 Kg (0.2 mole)}. The (lower layer) water layer was a 35.84% NaOH aqueous solution, tetrahydropyridazine was a trace. By the oxidation reaction, hydrazine hydrate, octahydropyridazino[1,2-a] pyridazine, and 1,1-bipyrrolidine contained in the simple distillation fraction were almost decomposed. The oxidation reaction yield was 59.3%.

Next, 4761.90 g of (upper layer) the tetrahydropyridazine layer {composition: tetrahydropyridazine 39.25% by weight, 1869.05 g (22.219 moles), 1-aminopyrrolidine 6.46% by weight, 307.62 g (3.571 moles), $H_2O$ and others 2585.24 g} was charged with a 5-liter four-necked flask, and was subjected to percise distillation by using a distillation tower. As a fraction, initial fraction: 407.6 g composition $H_2O$>99%, top 45–46° C., bottom 70–88° C., 100→95 mmHg, intermediate fraction: 490.4 g a mixture of, $H_2O$, 1-aminopyrrolidine and tetrahydropyridazine, top 49–69° C., bottom 84–98° C., 95→22 mmHg, main fraction: 1614.0 g composition tetrahydropyridazine>98%, top 42–60° C., bottom 74–90° C., 22→11 mmHg. The distillation yield of tetrahydropyridazine in the main fraction in the above procedure was 85.0%.

Example 35
Synthesis of tetrahydropyridazine

To 43.0 g (0.10 mole) of a 20% aqueous solution of 1-aminopyrrolidine was added 10.2 g (0.10 mole) of 36% HCl dropwise. An aqueous solution of 1-aminopyrrolidine hydrochloric acid salt was heated to 70° C., and 7.7 g (0.11 mole) of chlorine gas was blown into the above solution. The aqueous solution was stirred at 70° C. for 1 hour, cooled to room temperature, and the reaction solution (59.8 g) was quantitatively analyzed (GC).

The results were as follows: Tetrahydropyridazine 3.05% by weight, 1.82 g (0.022 mole), 1-aminopyrrolidine 5.28% by weight, 3.16 g (0.037 mole),the yield of tetrahydropyridazine 22.0%, and the conversion of 1-aminopyrrolidine 63.0%.

Example 36
Synthesis of tetrahydropyridazine

To 9.5 g (0.022 mole) of a 20% 1-aminopyrrolidine/toluene solution was added dropwise 74.0 g (0.024 mole) of 5.41% by weight m-chloroperbenzoic acid (MCPB)/toluene solution in a nitrogen atmosphere over the course of 30 minutes. After the addition, the reaction solution was stirred at room temperature for 1 hour, and 83.5 g of the reaction solution was quantitatively analyzed (GC).

The results were as follows: Tetrahydropyridazine 0.68% by weight, 0.57 g (0.0067 mole), 1-aminopyrrolidine 0.70% by weight, 0.58 g (0.0068 mole), the yield of tetrahydropyridazine 30.5%, and the conversion of 1-aminopyrrolidine 69.1%.

Comparative Example 1
Synthesis of hexahydropyridazine

A reactor was charged with 0.0675 g of 5% palladium/carbon and 3.9 g of methanol, hydrogen substitution was carried out, and the catalyst was activated. Then, 2.8 g of a tetrahydropyridazine methanol solution [composition: tetrahydropyridazine 23.77% by weight, 0.67 g (0.008 mole), pyrrolidine 1.61% by weight, 0.05 g (0.0006 mole), 1-aminopyrrolidine 1.36% by weight, 0.04 g (0.0004 mole)] was added to adjust it to a 10% by weight methanol solution of tetrahydropyridazine. Thereafter, at room temperature, a catalytic hydrogenation reaction was carried out under a normal pressure for 5 days. After the reaction, the reaction solution was analyzed by GC. The results were as follows: Hexahydropyridazine 46.98%, tetrahydropyridazine 22.84%, 1-aminopyrrolidine 23.89%, and pyrrolidine 3.91%, and the formation of hexahydropyridazine as the intended product was confirmed. The reaction selectivity was hexahydropyridazine 60.89%, 1-aminopyrrolidine 30.96%, and the conversion of tetrahydropyridazine was 77.16%. Incidentally, 1-aminopyrrolizine was formed from tetrahydropyridazine by a reduction side reaction, and the formation of pyrrolidine as a decomposition product was recognized.

Comparative Example 2
Synthesis of hexahydropyridazine

A reactor was charged with 0.0665 g of 5% platinum/carbon and 3.9 g of methanol, hydrogen substitution was carried out, and the catalyst was activated. Then, 2.8 g of a methanol solution of tetrahydropyridazine [composition: tetrahydropyridazine 23.77% by weight, 0.67 g (0.008 mole), pyrrolidine 1.16% by weight, 0.05 g (0.0006 mole), 1-aminopyrrolidine 1.36% by weight, 0.04 g (0.0004 mole)] was added to adjust it to a 10% by weight methanol solution of tetrahydropyridazine. Thereafter, a catalytic hydrogenation reaction was carried out at room temperature under a normal pressure for 5 days. After the reaction, the reaction solution was analyzed by GC. The results were as follows: Hexahydropyridazine 14.48%, tetrahydropyridazine 59.47%, 1-aminopyrrolidine 15.84%, pyrrolidine 9.78%, and the formation of hexahydropyridazine as the intended product was confirmed. The reaction selectivity was hexahydropyridazine 35.73%, 1-aminopyrrolidine 39.08%, and the yield of tetrahydropyridazine was 40.53%.

Comparative Example 3
Synthesis of hexahydropyridazine

A 1-liter glass autoclave was charged with 15.39 g of 5% palladium/carbon, and 259.8 g of a methanol solution of tetrahydropyridazine [composition: tetrahydropyridazine 23.77% by weight, 61.8 g (0.735 mole, pyrrolidine 1.61% by weight, 4.18 g (0.0588 mole), 1-aminopyrrolidine 1.36% by weight, 3.53 g (0.0414 mole)], and a catalytic hydrogenation reaction was carried out at 50° C. under a pressure of 9 Kg/cm$^2$G for 6 hours. After the reaction, the reaction solution was analyzed by GC, and the results were as follows: hexahydropyridazine 64.48%, tetrahydropyridazine 1.71%, 1-aminopyrrolidine 30.01%, pyrrolidine 3.42%. The reaction selectivity was hexahydropyridazine 65.60%, 1-aminopyrrolidine 30.53%, and the yield of tetrahydropyridazine was 98.29%.

The noble metal catalyst in the reaction solution was filtered and separated, and by using a distillation tower packed with Helipack, the methanol was recovered under normal pressure. Under reduced pressure, the residue was precisely distilled to isolate 15.7 g of a distillation fraction containing tetrahydropyridazine at 64–65° C. and under 30 mmHg. The composition of the fraction contained 98.40% of hexahydropyridazine, 0.07% of pyrrolidine, 0.16% of 1-aminopyrrolidine and 0.73% of tetrahydropyridazine (GC area percent). Incidentally, the structure of hexahydropyridazine was confirmed by NMR.

$^1$H-NMR (CDCl$_3$); 1.50–1.71 (m, 4H, —CH$_2$—); 2.85–3.22 (m, 4H, —CH$_2$—); 3.37 (s, 2H, —NH—)~D exchangeable

Example 37
Synthesis of hexahydropyridazine

A 100 ml. zirconium autoclave was charged with 0.2 g of 5% palladium/carbon, 18.8 g of methanol, 2.2 g (0.0262 mole) of tetrahydropyridazine and 0.2 g of a 38% aqueous solution of sodium hydroxide, and a catalytic hydrogenation reaction was carried out at 50° C. under a pressure of 9 Kg/cm$^2$ for 6 hours. After the reaction, the reaction solution was analyzed by GC. The results were as follows: hexahydropyridazine 44.85%, tetrahydropyridazine 52.78%, 1-aminopyrrolidine 1.36%. The reaction selectivity was hexahydropyridazine 94.98% and 1-aminopyrrolidine 2.88%, and the conversion of tetrahydropyridazine was 47.22%.

Example 38
Synthesis of hexahydropyridazine

A 100 ml. zirconium autoclave was charged with 0.2 g of 5% palladium/carbon, 18.8 g of methanol, 2.2 g (0.0262 mole) of tetrahydropyridazine and 0.2 g of a 38% aqueous solution of sodium hydroxide, and a catalytic hydrogenation reaction was carried out at 100° C. under a pressure of 9 Kg/cm$^2$G for 6 hours. After the reaction, the reaction solution was analyzed by GC. The results were as follows: hexahydropyridazine 86.99%, tetrahydropyridazine 8.37% and 1-aminopyrrolidine 3.54%. The reaction selectivity of hexahydropyridazine was 94.94%, and the reaction selectivity of 1-aminopyrrolidine was 3.86%, and the conversion of tetrahydropyridazine was 91.63%. The selective formation of hexahydropyridazine was confirmed by the existence of a small amount of sodium hydroxide.

What is claimed is:

1. A process for producing a compound expressed by the following formula (4):

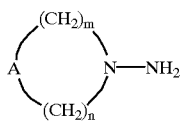
(4)

wherein "A" is an oxygen atom, a methylene group or an ethylidene group, and "m" and "n" respectively represent an integer of 1 to 3.
or its salt with a hydrohalogenide, which comprises
  reacting a hydrazine hydromonohalogenic acid salt expressed by the following formula (1):

NH$_2$NH$_2$—HX (1)

wherein "X" represents a halogen atom, with a diol compound expressed by the following formula (2):

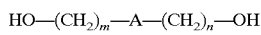
HO—(CH$_2$)$_m$—A—(CH$_2$)$_n$—OH (2)

wherein "A" is an oxygen atom, a methylene group or an ethylidene group, and "m" and "n" respectively represent an integer of 1 to 3,
in the presence of an excessive hydrohalogenic acid existing in a free form or in the form of an acid addition salt.

2. A process for producing a compound expressed by the following formula (4'):

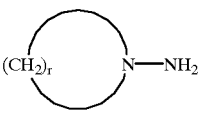
(4')

wherein "r" is an integer of 4 or 5,
or its salt with a hydrohalogenide, which comprises
  reacting a hydrazine hydromonohalogenic acid salt expressed by the following formula (1):

NH$_2$NH$_2$.HX (1)

wherein "X" represents a halogen atom,
with a compound expressed by the following formula (3):

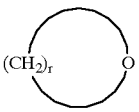
(3)

wherein "r" is an integer of 4 or 5, in the presence of an excessive hydrohalogenic acid existing in a free form or in the form of an acid addition salt.

3. A process according to claim 1 wherein the diol compound is 1,4-butanediol, and the the compound of formula (4) is 1-aminopyrrolidine.

4. A process according to claim 1 wherein the excessive hydrohalogenic acid is a hydrochloric acid or a hydrobromic acid.

5. A process according to claim 1 wherein the reaction is carried out in a mole ratio of the diol compound: the hydrazine hydromonohalogenic acid salt: the excessive hydrohalogenic acid=1:1–10:0.2–3 at a temperature of 100 to 150° C. under an elevated pressure.

6. A process according to claim 1 wherein the resulting reaction solution is concentrated, an alcohol solvent is added, the unreacted hydrazine hydrohalogenic acid salt precipitated as a crystal is removed, the separated mother liquor is treated to precipitate as a crystal, the precipitated hydrazine derivative hydrohalogenic acid salt is separated or recovered, or the separated mother liquor is neutralized with a base and distilled to obtain the hydrazine derivative.

7. A process according to claim 2 wherein the compound of formula (3) is tetrahydrofuran, and the alicyclic hydrazine derivative is 1-aminopyrrolidine.

8. A process according to claim 2 wherein the excessive hydrohalogenic acid is a hydrochloric acid or a hydrobromic acid.

9. A process according to claim 2 wherein the reaction is carried out in a mole ratio of the compound of formula (3): the hydrazine hydromonohalogenic acid salt: the excessive hydrohalogenic acid=1:1–10:0.2–3 at a temperature of 100 to 150° C. under an elevated pressure.

10. A process according to claim 2 wherein the resulting reaction solution is concentrated, an alcohol solvent is added, the unreacted hydrazine hydrohalogenic acid salt precipitated as a crystal is removed, the separated mother liquor is treated to precipitate as a crystal, the precipitated hydrazine derivative hydrohalogenic acid salt is separated or recovered, or the separated mother liquor is neutralized with a base and distilled to obtain the hydrazine derivative.

* * * * *